United States Patent
Gilchrist et al.

[11] Patent Number: 6,093,465
[45] Date of Patent: Jul. 25, 2000

[54] SELF-ADHESIVE LAMINATE

[75] Inventors: Thomas Gilchrist; David Michael Healy, both of Ayr, United Kingdom

[73] Assignee: Giltech Limited, Ayr, United Kingdom

[21] Appl. No.: 08/914,849

[22] Filed: Aug. 18, 1997

Related U.S. Application Data

[63] Continuation of application No. 08/556,919, filed as application No. PCT/GB94/01058, May 18, 1994, abandoned.

[30] Foreign Application Priority Data

May 18, 1993 [GB] United Kingdom ............ 9310185

[51] Int. Cl.[7] ............................................. A61F 13/00
[52] U.S. Cl. ................... 428/40.1; 428/42.1; 428/43; 428/138; 428/192; 428/194; 602/41; 602/52; 602/57; 602/58; 602/59; 602/60; 602/900
[58] Field of Search ............................... 428/40.1, 41.7, 428/41.8, 42.2, 43, 138, 192, 194; 602/41, 52, 59, 57, 58, 60, 900

[56] References Cited

U.S. PATENT DOCUMENTS

| | | | |
|---|---|---|---|
| 4,023,292 | 5/1977 | Shibata | 428/41.7 |
| 4,265,234 | 5/1981 | Schaar | 602/57 |
| 4,420,519 | 12/1983 | Slemmons | 428/41.7 |
| 4,513,739 | 4/1985 | Johns | 602/57 |
| 4,539,237 | 9/1985 | Clayton | 428/41.7 |
| 4,573,996 | 3/1986 | Kwiatek et al. | 604/897 |
| 4,744,355 | 5/1988 | Faassee, Jr. | 604/23 |
| 4,915,102 | 4/1990 | Kwiatek et al. | 128/156 |
| 5,415,627 | 5/1995 | Rasmussen | 602/57 |
| 5,437,662 | 8/1995 | Nardella | 606/40 |

FOREIGN PATENT DOCUMENTS

| | | |
|---|---|---|
| 0 081 990 | 6/1983 | European Pat. Off. . |
| 0 308 122 | 3/1989 | European Pat. Off. . |
| 0 356 614 | 3/1990 | European Pat. Off. . |
| 0 424 165 | 4/1991 | European Pat. Off. . |
| 0 520 330 | 12/1992 | European Pat. Off. . |
| 568401 | 3/1993 | European Pat. Off. . |
| 2711056 | 4/1995 | France . |
| 1 389 046 | 4/1975 | United Kingdom . |
| 9001915 | 8/1990 | WIPO . |

OTHER PUBLICATIONS

International Search Report dated Oct. 13, 1994.
"Safe and sound—Tegaderm I.V. transparent cannula dressing." ©3M Health Care 1988.
"OpSite IV 3000 Moisture Responsive Cannula Dressing." Smith and Nephew Medical Limited.
"NDM® Wound Care Products." ©1992 NDM Corporation.
"KALTOCLUDE." Britcair Limited.
"Semipermeable Film Dressings." Chapter 4, pp. 25–34.

*Primary Examiner*—Nasser Ahmad
*Attorney, Agent, or Firm*—Ratner & Prestia

[57] ABSTRACT

A medical film dressing comprising a thin transparent film having a layer of skin adhesive on its front face, shielded before use by a removable cover sheet in contact which is in contact with the adhesive across the entire area of the front face, and a backing sheet detachably affixed over the whole of the rear face of said film. The dressing further comprises a flexible hinge in the form of a folded strip disposed along a peripheral edge of said thin film to conjoin said cover sheet and said backing sheet adjacent said edge, and extending around the corresponding edge of the thin film, and wherein a scoreline is formed in said cover sheet. The score line extends parallel to the edge of the dressing opposite the hinge and wherein the line of perforation extends through said thin film beneath said score line.

10 Claims, 1 Drawing Sheet

SELF-ADHESIVE LAMINATE

This application is a continuation of application Ser. No. 08/556,919 filed Nov. 20, 1995, now abandoned filed as a 371 of PCT/GB94/01058, filed on May 18, 1994.

This invention relates to a laminate, and relates especially but not exclusively to a dressing which is self-adherent to body surfaces around a wound.

BACKGROUND TO THE INVENTION

In recent years laminates for use as wound dressings have become available which are based on polyurethane films. The film may contain or act as a carrier for substances such as silver salts or alginates which act as bacteriostats or which promote healing.

Film dressings of this nature have considerable advantages in two respects. First, they can readily be produced in transparent form and thus allow the condition of the wound to be monitored without removing the dressing. Secondly, they can be produced in microporous forms which allow movement of water vapour to the exterior of the dressing and movement of air to the interior of the dressing, while preventing movement of bacteria through the dressing; this is of benefit in treating exuding wounds such as burns.

Film dressings presently in use, however, have the disadvantage that they are difficult to apply. It is usual for a film dressing to have an adhesive layer for application to the skin of the patient, the adhesive layer being initially covered by a release paper. Once the release paper is removed from the adhesive layer, the film is delicate and difficult to handle. Stretching of the film can destroy its barrier integrity, while a lack of tension during application can lead to wrinkling. For these reasons, most film dressings currently used are provided with a stiffened edge or frame on the outer face, which stiffening must be removed after the dressing has been applied. These arrangements, however, lead to undesirable complexity, waste of material, and increased expense.

SUMMARY OF THE INVENTION

According to a first aspect of the present invention there is provided a laminate comprising a carrier sheet presenting an adhesive front face, a cover sheet covering said adhesive front face, said cover sheet being of a material which can be removed from the front face without substantially reducing the adhesiveness of the front face, a backing sheet detachably affixed on the rear face of said carrier sheet, and a flexible hinge disposed along a peripheral edge of said carrier sheet to conjoin said cover sheet and said backing sheet adjacent said edge.

Preferably, when the laminate is a wound dressing the carrier sheet is formed of a polymeric film material which is porous to water vapour and air but which is substantially impermeable to micro-organisms and pathogens, said polymeric film material most preferably being polyurethane.

Preferably, the cover sheet is penetrated by a score line which is preferably substantially parallel to but remote from said hinge member to provide a readily accessible edge to initiate peeling of the cover sheet from the carrier sheet. Said score line is preferably located adjacent an edge of the cover sheet which is opposite the edge of the cover sheet along which the hinge is disposed.

The backing sheet can, if desired, be held on the carrier sheet by a separate adhesive material, or may be held thereon through adhesion between the material of the backing sheet and the material of the carrier sheet.

The backing sheet is preferably affixed to the rear face of the carrier sheet with an adhesiveness which is less than the adhesiveness between the front face of the carrier sheet and the cover sheet or, when the laminate is a wound dressing, between the front face of the carrier sheet and body tissue, such as human skin, to which the dressing is to be applied.

The hinge may be constituted by an initially separate member which is secured to the cover sheet and to the backing sheet in the course of fabricating the laminate. The hinge member may be formed of a flexible tape, suitably a polypropylene tape, and preferably a pressure-sensitive self-adhesive tape.

The carrier sheet, the cover sheet and the backing sheet are preferably all substantially transparent; this allows precise visual alignment of the laminate over a wound site when the laminate is a dressing.

The front face preferably carries an adhesive material, and this may contain a medicament, for example an alginate or other absorbent material, a bacteriostatic silver compound or other antibiotic, antiseptic or antibacterial material.

According to a second aspect of the present invention there is provided method of manufacturing a laminate, comprising providing a carrier sheet which has an adhesive front face, a cover sheet on said front face and a backing sheet detachably affixed on the rear face of said carrier sheet, and affixing a flexible hinge along one edge of the cover sheet and the backing sheet to extend around the corresponding edge of the carrier sheet.

Preferably a score line is formed along and adjacent an edge of said cover sheet remote from said hinge.

The hinge may be provided by a tape which may be polypropylene and which is preferably self-adhesive.

BRIEF DESCRIPTION OF THE DRAWINGS

Embodiments of the present invention will now be described, by way of example only, with reference to the accompanying drawings, in which.

DESCRIPTION OF PREFERRED EMBODIMENTS

Figure 1:
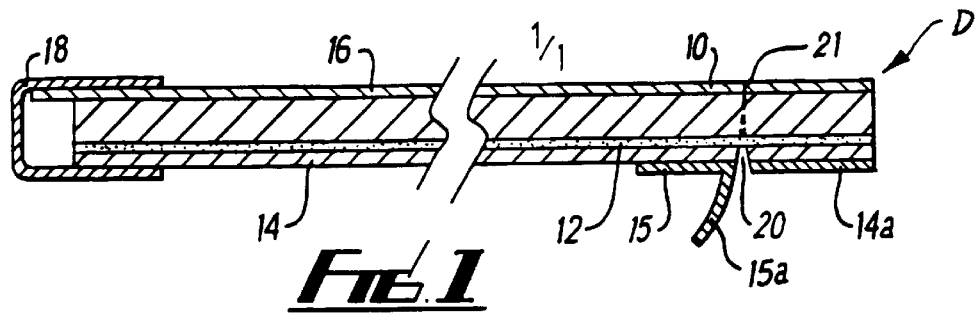
FIG. 1 is a cross-section of a laminate in the form of a wound dressing embodying the present invention, prior to use of the dressing.

Referring to FIG. 1, a laminate is in the form of a dressing D which comprises a carrier sheet 10 in the form of a transparent and permeable polyurethane film. The front face of the film 10 (the lower face as viewed in FIG. 1) is coated with an adhesive layer 12 which may be of any adhesive material suitable for use on human skin; in this embodiment the material is a pressure-sensitive solvent-based acrylic compound. The adhesive material of the layer 12 and the polyurethane film 10 are both in admixture with a bacteriostatic silver compound such as a soluble glass containing silver orthophosphate. The layer 12 is covered by a cover sheet 14 which is a transparent polymer sheet held in place by the adhesive layer 12. The right edge of the cover sheet 14 (as viewed in FIG. 1) is provided on its outer face with a holding tab 14a, and immediately in from the tab 14a, the sheet 14 is also provided with a pull tab 15 having a free-standing extension flap 15a. The rear face of the film 10 (the upper face as viewed in FIG. 1) is covered by a backing sheet 16 which adheres to the film 10 with an adhesiveness which is lower than that between the film 10 and the layer 12. The relatively lower tack between the rear face of the film 10 and the backing sheet 16 ensures that when the dressing is applied, with the cover sheet 14 removed, from the front face of the film 10, to a patient's skin and the backing sheet 16 is pulled, the backing sheet 16 separates from the film 10 while the relatively higher tack of the adhesive of the layer 12 continues to hold the film 10 on to the body tissue of the patient. The backing sheet 16 is of a transparent polymer film, but other materials such as siliconised paper may alternatively be used for the backing sheet.

The laminate of the cover sheet 14, the film 10 and the backing sheet 16 as described above is available in manufactured strip form from, for example, the Rexham division of Bowater plc.

One edge of the dressing D (the left edge as viewed in FIG. 1) is cut away through the cover sheet 14, the adhesive layer 12 and the film 10, but leaving the backing sheet 16 intact across its original width. This partially cut-away edge of the dressing D is then provided with a hinge member 18 in the form of a folded strip secured both to the outer surface of the cover sheet 14 and to the outer surface of the backing sheet 16. The strip 18 may suitably be of self-adhesive polypropylene tape which is preferably pressure sensitive.

Figure 2:
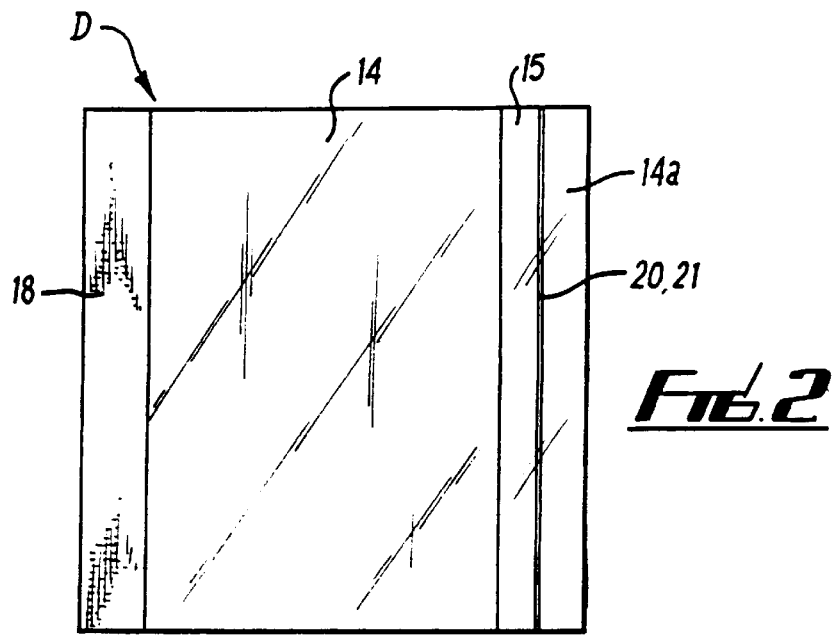
FIG. 2 is a front view, to a smaller scale, of the dressing of FIG. 1.
Figure 3:
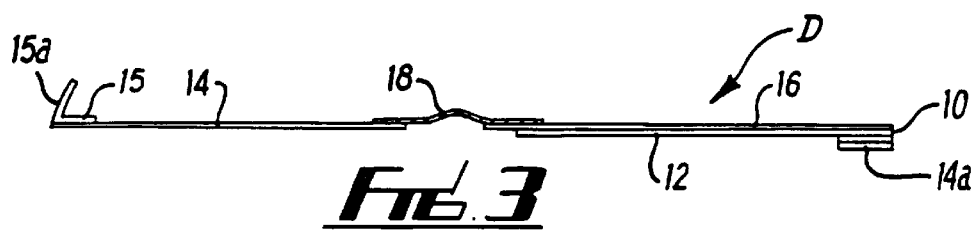
FIG. 3 is a view similar to FIG. 1 of the same dressing as prepared for use and immediately prior to application.

A score line 20 is formed through the cover sheet 14 adjacent and parallel to the edge of the dressing D opposite the hinge member 18, between the holding tab 14a and the pull tab 15 (avoiding the pull tab extension flap 15a). A line of perforations 21 is formed completely through the dressing D below the score line 20 from the same (lower) face of the dressing D as the score line 20 is formed. The relative disposition of the hinge member 18, the score line 20 and the tabs 14a and 15 will be seen from FIG. 2. It is to be noted that the relative thicknesses of the various layers shown in FIGS. 1 and 3 are not necessarily to scale.

In use, the dressing D is supplied sterile in a sealed pouch (not shown). At the time and place of use of the dressing D, the pouch is opened, the dressing D is removed from the pouch and grasped by the holding tab 14a, and bent around the score line 20, which raises an adjacent edge of the main portion of the cover sheet 14 under the tab 15. The extension flap 15a is gripped by the user who can then peel the cover sheet 14 away from the adhesive layer 12 while holding the tab 14a on the opposite edge. The cover sheet 14 remains attached to the hinge member 18 and can therefore be hinged through 180 degrees to the configuration shown in FIG. 3.

The dressing D is then applied over a wound or other application site and pressed into place on the body tissue around the wound. During this operation, the backing sheet 16 maintains the film 10 in a dimensionally stable and readily handled condition, allowing the dressing to be secured to the body tissue around the wound or other application site without creasing or stretching of the film 10.

Thereafter, by pulling on the flap 15a attached to the cover sheet 14 to the right, the hinge member 18 and the backing sheet 16 are conjointly removed from the film 10. The right edge portions of the dressing D under the holding tab 14a are removed from the film 10 by tearing along the perforations 21 after application of the main portion of the dressing D to the patient, the overlying edge of the film 10 subsequently being smoothed down onto the body tissue of the patient. The film 10 conforms well to the underlying tissue surface because the dressing D is flexible in two directions, i.e length and width. The act of peeling the cover sheet 14 away from the film 10 automatically takes the user's hands away from the face of the dressing D which will be applied to the patient's tissue, thus avoiding contact which would be potentially contaminating. As an alternative to removing the right edge portions by tearing along the perforations 21, this edge of the dressing D could be cut off with scissors after application of the main portion of the dressing D to the patient.

The dressing D may be readily manufactured. It is known to make film dressing material in bulk by laminating polyurethane film with adhesive and release layers. A dressing of the present invention can be made by slitting such bulk material to the desired width for individual dressings, folding self-adhesive polypropylene tape and pressing it to one edge to form the hinge, cutting the score line (for example by a rotary knife), and cutting the resulting strip across its width at suitable regular intervals to form individual dressings.

An example of a bulk film dressing material consists of a lamination of:

sPET1/PUf/PSA/sPET2 where:

| | |
|---|---|
| sPET1 and sPET2 = | siliconised polyethylene terephthalate having different silicone linearisations; |
| PUf = | polyurethane film; |
| PSA = | pressure sensitive adhesive. |

The PUf (polyurethane film) may be impregnated with a silver-releasing product as a bacteriostat.

A grid pattern (not illustrated) may be printed onto the backing sheet 16 for monitoring wound size. After application of the film 10 but prior to removal of the backing sheet 16, the outline of the wound can be traced onto the backing sheet. The area of the wound can subsequently be calculated from the outline on the grid, which is also suitable to be retained as a record as it is not contaminated by contact with the wound, having been spaced from the wound by the intervening polyurethane film 10.

Instructions for use of the dressing can be printed on the tabs 14a and 15, as can advertisements and/or other messages.

Islands of alginate or other absorbent material can be pre-located in the centre of the dressing D as an aid to healing.

As an alternative to a wound dressing, the invention may be utilised as a transdermal medicament delivery system, for example as nicotine supply patches, or, as a non-medical application in the electronics industry.

The above described embodiment of the present invention provides a novel dressing having a number of advantages:

the dressing is protected against stretching during application;

the dressing is protected against creasing during application;

the dressing is not touched by the user during application, reducing problems of contamination;

the amount of waste material is reduced;

the dressing conforms well to uneven surfaces as it is flexible in two directions, i.e. length and width;

single handed application is possible;

manufacture is simple and a wide range of sizes can readily be produced; for example, the depth of the score line once set provides accurately repeatable performance;

the whole of the dressing is transparent thus allowing the user to see exactly where it is being applied.

Figure 4:
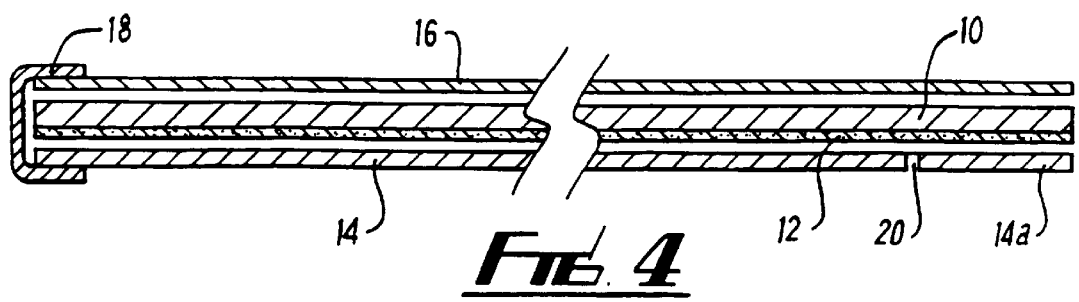
FIG. 4 is an exploded cross-section of a second embodiment of the invention.

FIG. 4 shows an alternative form of laminate in accordance with the invention. The general construction is similar to that of the laminate of FIG. 1, but the perforation 21, the pull tab 15 and extension flap 15a are absent. In addition, the left edges of the backing sheet 16, the film 10, the adhesive layer 12 and the cover sheet 14 are coterminous adjacent the hinge 18.

Modifications may be made to the above-mentioned embodiment without departing from the scope of the invention as defined in the appended claims.

We claim:

1. A medical film dressing comprising a dimensionally unstable flexible thin film presenting a front face and a rear face, the front face having an adhesive coating, a cover sheet covering said front face and in contact with said adhesive across substantially the entire area of the front face, said cover sheet being of a material which can be removed from the front face without substantially reducing the adhesiveness of the front face, a backing sheet detachably affixed over the whole of the rear face of said thin film and imparting dimensional stability to said thin film, and a flexible hinge in the form of a folded strip disposed along a peripheral edge of said thin film to conjoin said cover sheet and said backing sheet adjacent said edge, and extending around the corresponding edge of the thin film, and wherein a score line is formed in said cover sheet, the score line extending parallel to the edge of the dressing opposite the hinge and wherein a line of perforations extend through said thin film beneath said score line.

2. A medical dressing as claimed in claim 1, wherein said score line is substantially parallel to but remote from said hinge member.

3. A medical dressing as claimed in claim 2, wherein said score line is located adjacent an edge of said cover sheet which is opposite the edge of said cover sheet along which said hinge is disposed.

4. A medical dressing as claimed in claim 1, wherein said backing sheet is affixed to said rear face of said carrier sheet with an adhesiveness which is less than the adhesiveness between the carrier sheet and the cover sheet.

5. A medical dressing as claimed in claim 1, wherein said backing sheet is affixed to the rear face of the carrier sheet with an adhesiveness which is less than the adhensiveness between the front face of the carrier sheet and human skin.

6. A medical dressing as claimed in claim 1, wherein said hinge is constituted by an initially separate member which is secured to said cover sheet and to said backing sheet.

7. A medical dressing as claimed in claim 6, wherein said hinge member is formed of a flexible tape.

8. A medical dressing as claimed in claim 1, wherein said carrier sheet, said cover sheet and said backing sheet are all substantially transparent.

9. A method of manufacturing a medical dressing, comprising providing a carrier sheet which has an adhensive front face, a cover sheet on said front face and backing sheet which extends beyond the length of said carrier sheet and is detachably affixed on the rear face of said carrier sheet, affixing a flexible hinged along one edge of the cover sheet and the backing sheet to extend around the corresponding edge of the carrier sheet, and providing a score line in the cover sheet parallel to the edge of the dressing opposite the hinge and punching a line of perforations through the carrier sheet below said score line.

10. A method of manufacturing a film dressing, comprising providing a length of laminate with comprises a thin film having a front face and a rear face, the front face having an adhesive coating, a cover sheet covering said front face and in contact with said adhesive across substantially the entire area of said front face, the cover sheet being of a material which can be removed from the front face without substantially reducing the adhesiveness of the front face, and a backing sheet detachably affixed over the whole of the rear face of said thin film and imparting dimensional stability to the thin film, slitting said laminate to a desired width for said film dressing to produce a slit edge, affixing self-adhesive tape along the slit edge of the laminate to provide a flexible hinge extending from the face of the cover sheet remote from the thin film around an edge of the thin film, to face of the backing sheet remote from the thin film, cutting the resulting hinged laminate across its width, providing a score line in the cover sheet parallel to the edge of the dressing opposite the hinge and punching a line of perforations through the thin film below said score line.

* * * * *

UNITED STATES PATENT AND TRADEMARK OFFICE
CERTIFICATE OF CORRECTION

| | |
|---|---|
| PATENT NO. | : 6,093,465 |
| DATED | : July 25, 2000 |
| INVENTOR(S) | : Gilchrist et al. |

It is certified that error appears in the above-identified patent and that said Letters Patent is hereby corrected as shown below:

<u>Column 6,</u>
Line 15, should read: -- front face, a cover sheet on said front face and a backing sheet --
Lines 39 and 40, should read: -- from the thin film around an edge of the thin film, cutting the --

Signed and Sealed this

Twenty-third Day of October, 2001

Attest:

*Nicholas P. Godici*

NICHOLAS P. GODICI
*Attesting Officer*      *Acting Director of the United States Patent and Trademark Office*

UNITED STATES PATENT AND TRADEMARK OFFICE
CERTIFICATE OF CORRECTION

PATENT NO.    : 6,093,465
DATED         : July 25, 2000
INVENTOR(S)   : Gilchrist et al.

It is certified that error appears in the above-identified patent and that said Letters Patent is hereby corrected as shown below:

Column 6,
Line 15, should read -- front face, a cover sheet on said front face and a backing sheet --
Lines 39 and 40, should read -- from the thin film around an edge of the thin film, cutting the --

Signed and Sealed this

First Day of January, 2002

Attest:

JAMES E. ROGAN
Attesting Officer          Director of the United States Patent and Trademark Office